United States Patent [19]

Dodd

[11] Patent Number: 4,991,444

[45] Date of Patent: Feb. 12, 1991

[54] CENTRIFUGAL CARTON TEST METHOD AND APPARATUS

[75] Inventor: Clayton Dodd, West Monroe, La.

[73] Assignee: Manville Corporation, Denver, Colo.

[21] Appl. No.: 509,923

[22] Filed: Apr. 16, 1990

[51] Int. Cl.⁵ .............................................. G01N 3/00
[52] U.S. Cl. ................................................... 73/788
[58] Field of Search ................. 73/834, 827, 835, 838, 73/788

[56] References Cited

U.S. PATENT DOCUMENTS 4,553,438  11/1989  Dawson et al. ...................... 73/830

FOREIGN PATENT DOCUMENTS 1469304  3/1989  U.S.S.R. ............................... 73/788

*Primary Examiner*—Jerry W. Myracle
*Attorney, Agent, or Firm*—John D. Lister

[57] ABSTRACT

Testing open-ended cartons to determine the centrifugal force at which the contents will move out an open end. A filled carton is positioned on a support and the carton is gripped at the end portions of the carton side panels and rotated. Upon reaching a rotational speed at which the carton can no longer hold the contents in place, the contents strike an end wall of the support, indicating that the carton has failed.

13 Claims, 3 Drawing Sheets

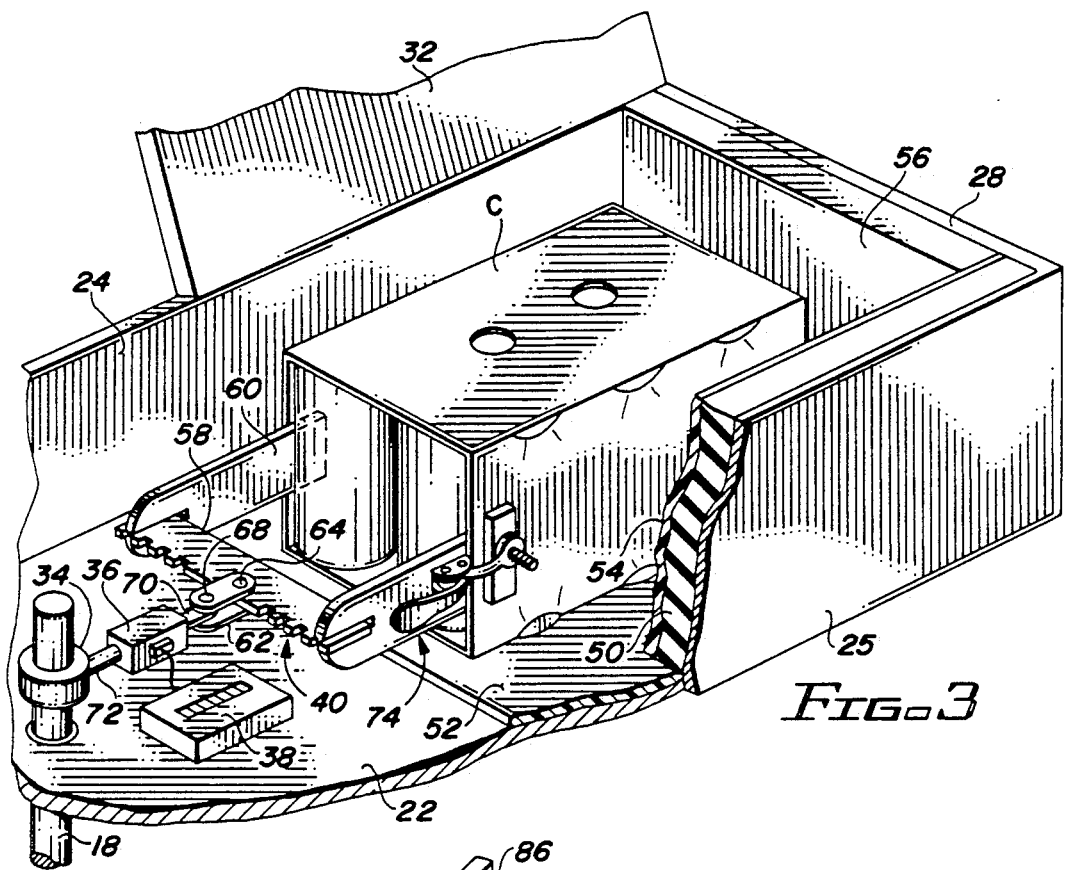
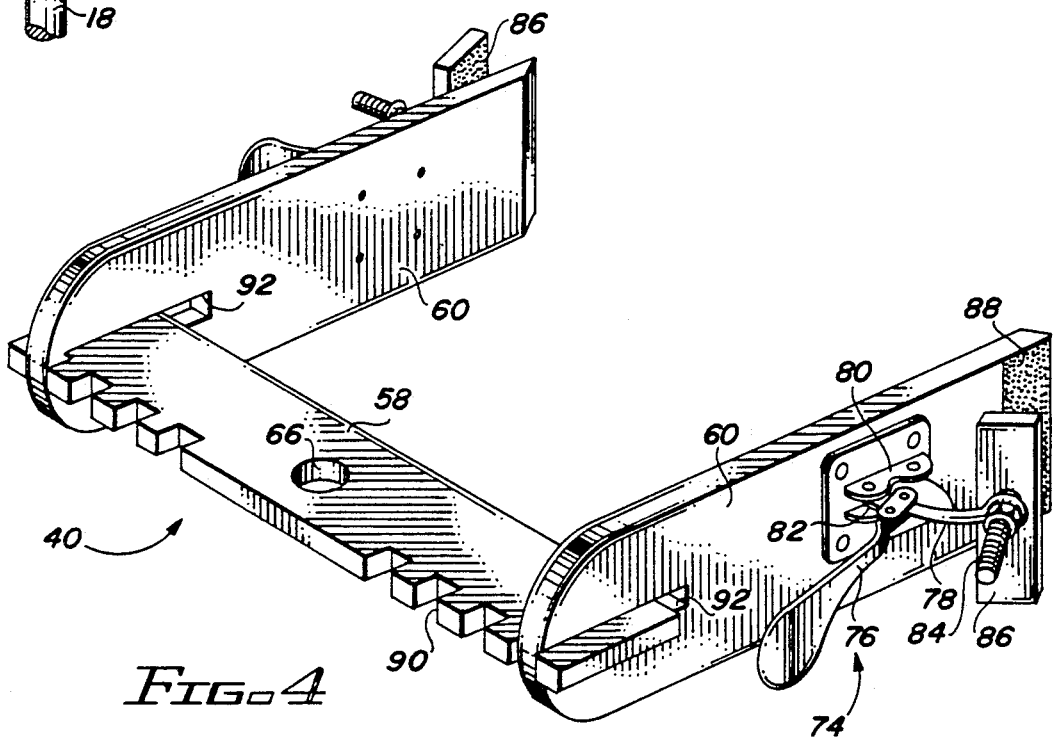

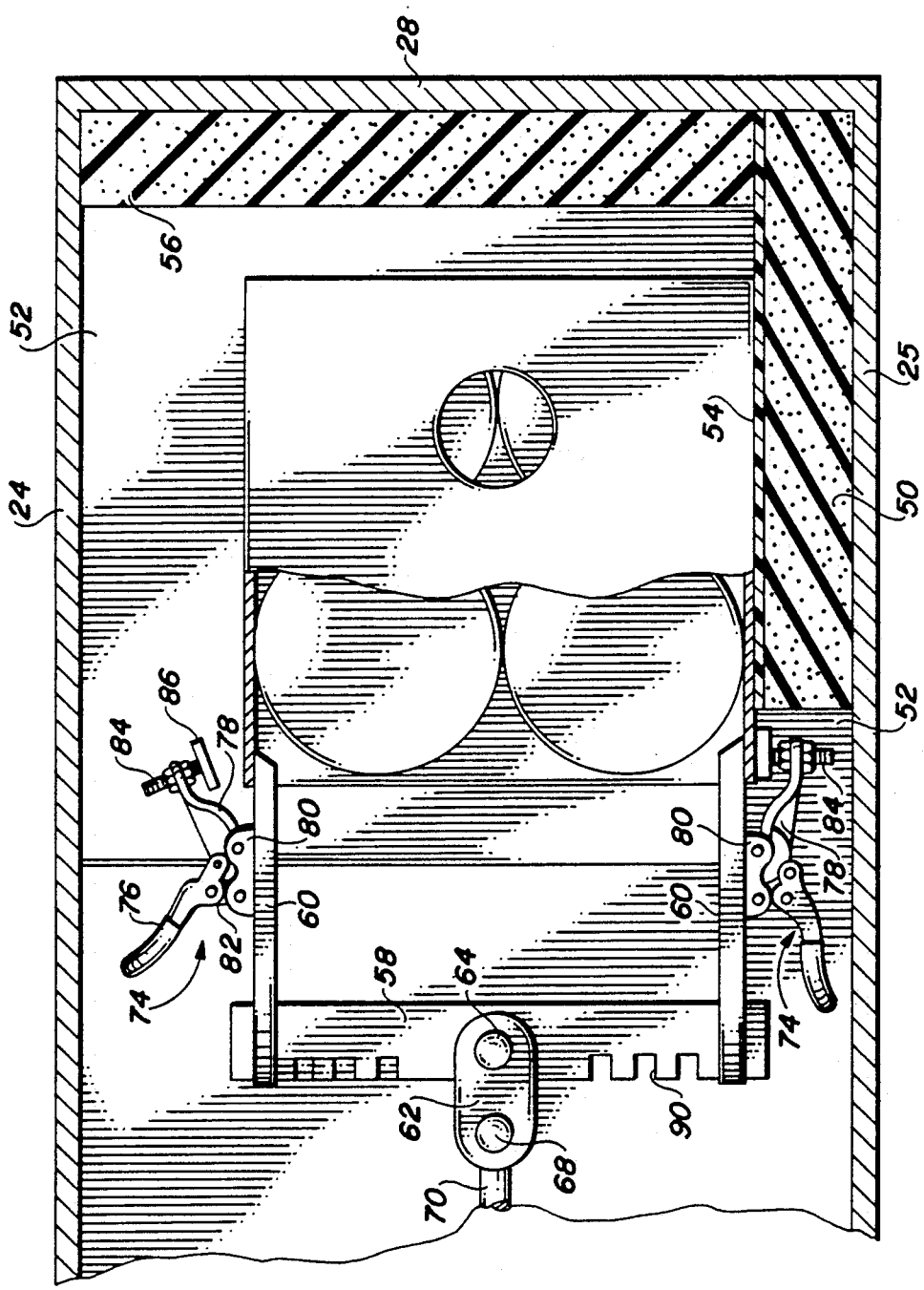

4,991,444

CENTRIFUGAL CARTON TEST METHOD AND APPARATUS

FIELD OF THE INVENTION

This invention relates to a carton test method and apparatus. More particularly, it relates to a centrifugal carton test method and apparatus for use with an open-ended article carrier.

BACKGROUND OF THE INVENTION

Paperboard carriers used to hold beverage cans and bottles must be strong enough to withstand the stresses of lifting, carrying and handling without tearing or separating. Because beverage containers are often quite heavy, it has become desirable to test carriers of new design to make sure they are able to remain intact during their life. For this reason testing methods and equipment have been devised to determine the failing point of carriers. This has also provided a reliable tool for use in quality control in the manufacture of the carriers and has enabled minimum physical standards to be established for carriers. An example of an effective centrifugal test device can be found in U.S. Pat. No. 4,553,438 which discloses a device for receiving a loaded carrier and connecting it to a force gauge by an attachment that fits into the handle of the carrier. When the carrier fails during rotation of the carrier support, either by tearing of the paperboard or separation of the mechanical or adhesive flap locking means, the beverage containers are thrown outwardly against an end wall on the support, and the force to which the carrier was subjected at this time is recorded on the gauge.

In addition to the failure of a carrier as the cause of its contents falling out, the contents of an open-ended carrier can also escape through an open end of the carrier, such as by rapidly swinging the carrier in an arc. Such carriers consist of top and bottom panels connected by side panels, with the ends of the carrier being open. The cans or bottles in the carrier are normally held in place by the carrier being tightly wrapped around them and by openings in the side panels through which portions of the container bottoms extend. In the case of cans, the side panels may also contain openings adjacent the top panel through which portions of the upper edges of the cans extend. Through unusually harsh handling or through normal handling of carriers which have been weakened by moist conditions, it is sometimes possible for the containers to be thrown out one of the open ends.

It would be desirable to be able to quantify the failure or inability of open-ended carriers to prevent their packaged containers from being thrown out an open end. The test apparatus described above, however, is not designed to carry out such a test procedure, nor is a suitable test method or test equipment available for this purpose. It is a main purpose of this invention to provide such a method and apparatus.

SUMMARY OF THE INVENTION

In accordance with the invention, a test apparatus is provided which comprises a support attached to a drive shaft capable of rotating at varying speeds. The support is adapted to receive an open-ended carrier or carton so that one open end faces the drive shaft and the other open end faces outwardly, allowing centrifugal force from the rotating support to cause the contents of the carton to move out the other open end. Gripping means are provided for gripping the carton so as not to interfere with the movement of the contents of the carton out the open end, and means are connected to the support and to the gripping means for measuring the force applied to the carton at the time the contents move out the other open end of the carton.

The gripping means preferably grips the end portions of the side panels of the carton located nearest the drive shaft, and the gripping means are designed to receive cartons of varying size. Preferably, the carton support has an end wall spaced from the end of the carton through which the contents are thrown, so that when the contents strike the end wall the force being applied to the carton at that time is the force at which the carton has failed. The support also includes means for receiving a counterweight at the other end of the support.

It will be understood that for the purpose of the invention, the terms "carrier" and "carton", as used in the specification and claims, may be considered equivalent.

The above and other aspects of the invention, as well as other benefits thereof, will readily be apparent from the more detailed description of the preferred embodiment which follows.

BRIEF DESCRIPTION OF THE DRAWINGS

FIG. 3 is a partial pictorial view of the testing device of the invention, showing a beverage container carrier supported in the device for testing;

FIG. 4 is an enlarged pictorial view of the clamp used for connecting a force gauge to a carrier; and FIG. 5 is an enlarged horizontal sectional view taken on line 5—5 of FIG. 2.

DETAILED DESCRIPTION OF THE PREFERRED EMBODIMENT

Figure 1:
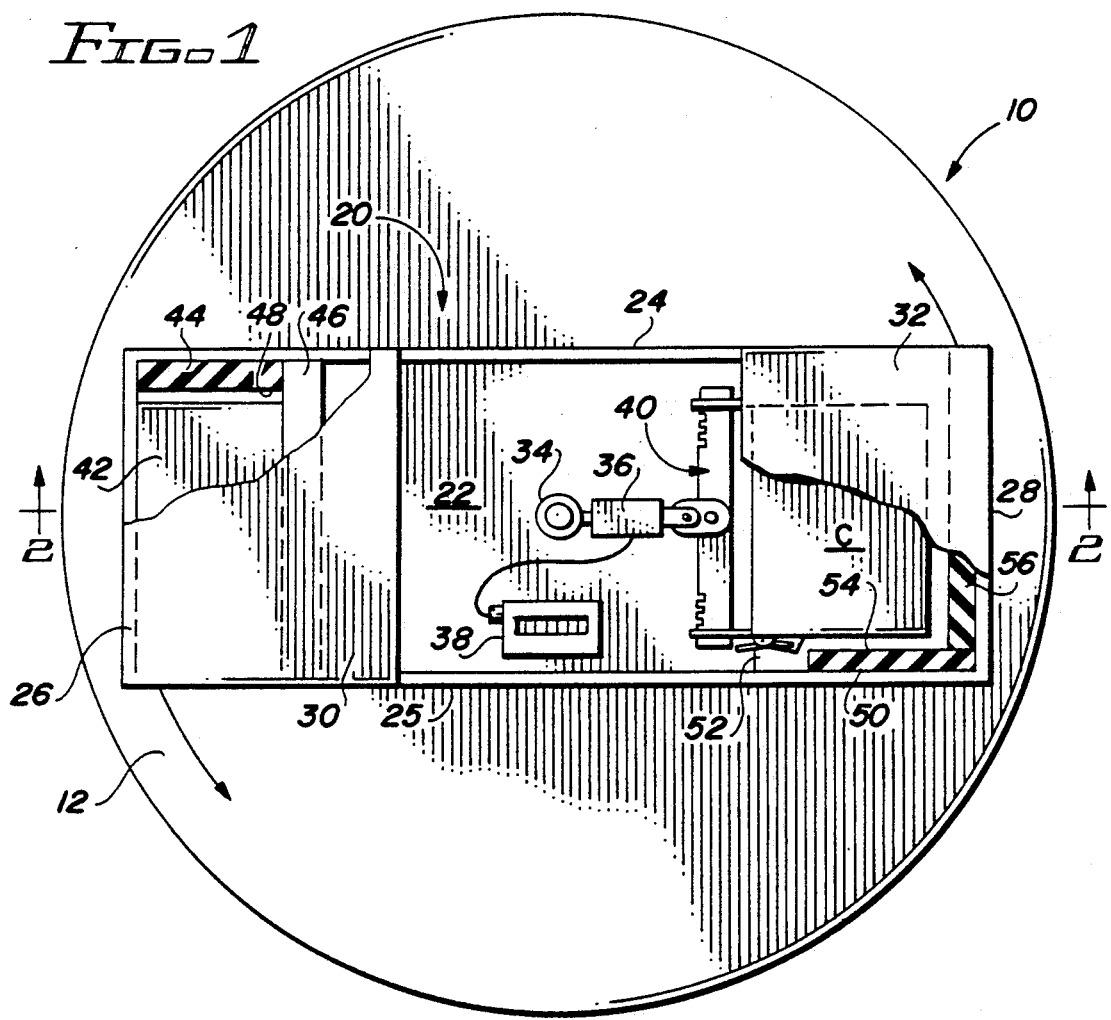
FIG. 1 is a plan view of the test apparatus of the present invention, with the lids located at the end of the rotating support structure being only partially shown for the sake of clarity.
Figure 2:
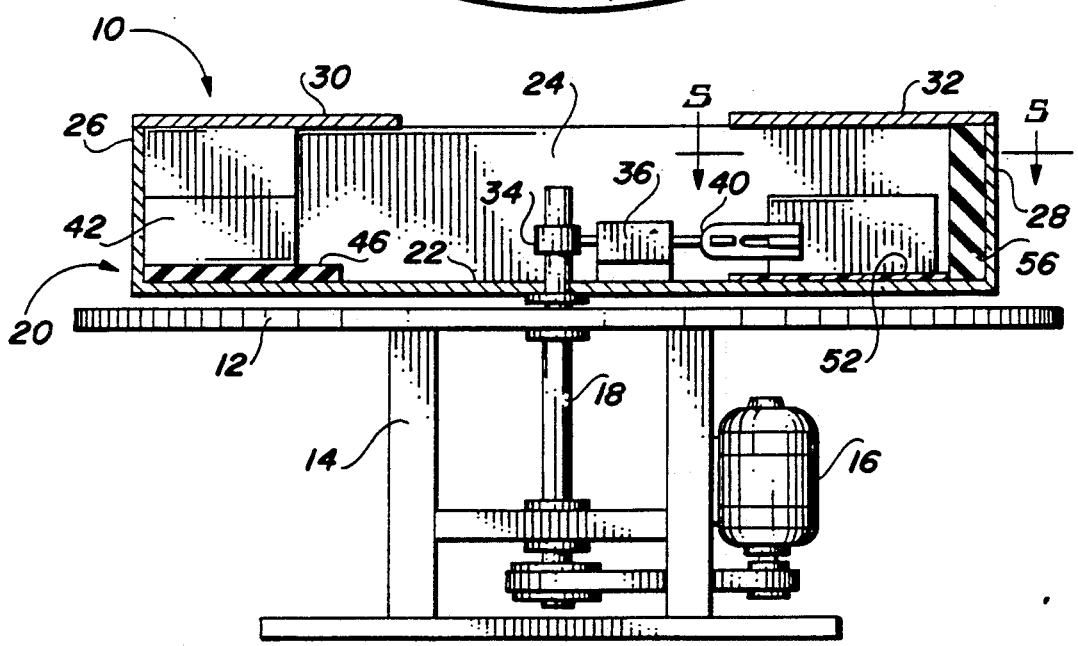
FIG. 2 is a transverse cross-sectional view of the apparatus taken along line 2—2 of FIG. 1.

Referring to FIGS. 1 and 2, the testing apparatus 10 comprises a stationary table 12 supported on legs 14. Mounted on support structure attached to the legs is a variable speed motor 16 for rotating vertical shaft 18. The vertical shaft 18 extends through suitable bearings mounted in an opening in the table 12 and is affixed to a rectangular box-like container 20 which is supported by the shaft 18 at its balance point above the table 12. The container 20 consists of a bottom wall 22, side walls 24 and 25, and end walls 26 and 28. The container 20 may be provided with a cover or, as shown in FIG. 2, with end covers 30 and 32.

Connected to the shaft 18 by suitable means such as collar 34 is a load cell 36 connected to a digital readout 38. The load cell, which may be of any suitable design capable of measuring the force applied to a test carton, is connected to clamp 40 which is attached to a carton C shown positioned in one end of the support container 20. A suitable counterweight 42 is positioned in the other end of the container 20 to balance the weight of the carton. A rubber pad 44 is positioned between the side wall 24, which may be considered as the trailing wall of the container 20 relative to the direction of rotation of the counterweight 42, and the counterweight 42. The pad acts to cushion the contact between the side wall 24 and the counterweight 42 and to center the counterweight in the container 20 between the two side walls. There is no need for any material between the counterweight and the side wall 25 because the rotational forces exerted on the counterweight will maintain it engaged with the pad 44 and spaced from the wall 25. A sheet 46 having a surface of reduced friction, such as a sheet formed of TEFLON, is provided beneath the counterweight to enable it to readily move into place as the container 20 rotates. A similar sheet 48 may also be provided between the counterweight and the pad 44 for the same purpose.

A pad 50 is provided at the interior of the side wall 25 adjacent the location for receiving a carton C, the side wall 25 being considered the trailing wall in relation to the carton during rotation of the container 20. As in the case of the counterweight 42 and the pad 44, the pad 50 functions to help center the carton and to cushion the contact between the side wall 25 and the carton. Sheets 52 and 54, having surfaces of reduced friction as in the case of sheets 46 and 48, are provided on the bottom wall of the container and adjacent the interior side of the pad 50 to facilitate movement of the carton into place and to facilitate movement of the contents of the carton as they are thrown out of the open end of the carrier adjacent the end wall 28. A rubber pad 56 is provided on the interior of the end wall 28 to cushion the impact of cans or bottles thrown out of a carton.

Referring now to FIGS. 3–5, the clamp 40 comprises a transverse support bar 58 attached to two clamp support arms 60. One end of a link 62 is connected to the support bar 58 by a pin 64 which extends through a centrally located opening 66 in the support bar. A pin 68 extending through the other end of the link 62 connects the link to a rod 70, which may take the form of an eyebolt, extending from the load cell 36. The load cell is further connected to the collar 34 mounted on the shaft 18 by rod 72. Obviously, any alternative convenient manner of connecting the clamp support bar to the load cell and the load cell to the shaft 18 may be used, if desired.

A clamp 74 is attached to the outer face of each of the clamp support arms 60. Although the clamp may take any convenient form, for ease in actuating it and for its ability to remain locked in clamped condition, the preferred clamps are those comprised of a handle arm 76 pivotally connected to a clamping arm 78, with the clamping arm 78 being pivotally connected to a horizontal support base 80 and the handle arm 76 being connected to the support base 80 through a link 82. Such a clamp is readily commercially available, as for example from Destaco Corporation. The clamp illustrated in the drawings is Destaco clamp No. 206-S.

The end portion of the clamp arm 78 contains a threaded opening through which threaded shaft 84 extends. The threaded shaft 84 carries a clamping plate 86 at its end which is adapted to engage the outer end face 88 of the clamp support arm 60. As shown in FIG. 4, the engaging faces of the plate 86 and the outer end face 88 of the clamp support arm may be roughened by any suitable means, as by gluing sandpaper to them, for example, to further enhance the grip of the clamp on a carton.

In operation, a counterweight selected to balance the loaded carton to be tested is placed in one end of the support 20 and the lid 30 is closed. The lid 30 may be connected to one of the side walls of the support 20 by hinges and may be secured in place at its other end by a suitable latch. The connections of the lid are not shown since their details do not form a part of the invention.

A fully loaded carrier or carton C is then placed in the other end of the support 20 with its side panels parallel to the side walls 24 and 25 of the support 20. This provides for one of the open ends of the carton to face the drive shaft 18 and the other open end to face the end wall of the support 20. The end portions of the side panels of the carton C are then clamped between the clamping surfaces 86 and 88, with the farthest open end of the carton being spaced from the pad 56 at the end wall 28 a distance which will enable the contents of the carton to be thrown against it when the carton is no longer able to hold its contents in place against the centrifugal force applied by the rotating support 20. Note that the clamping surfaces 86 and 88 are sufficiently narrow to permit them to grip the side panels of the carton without interfering with the contents of the carrier.

The clamp 40 is designed to accommodate cartons of varying widths by providing the support bar 58 with notches 90 on either side of the central opening 66 and by providing the adjacent end of each clamp support arm 60 with a slot 92. The clamp support arms can be moved along the support bar 58 to the notches 90 which permit the clamps to be aligned with the side panels of the test carton and locked in place by seating each clamp support arm in the base of the aligned notch.

After attaching the test carton in place and securing the clamp support bar 58 to the link 62, the lid 32 is then closed and latched, making the apparatus ready for the test to be conducted. The motor 16 is then caused to rotate the shaft 18 and the attached support structure 20 at increasing speeds until the carton is no longer able to hold its containers in place against the centrifugal force caused by rotation of the carton. When this occurs the containers, illustrated in FIGS. 3 and 5 as beverage cans, will be thrown toward the end wall 28 of the support 20. Because the carton is spaced a relatively short distance from the rubber pad 56, the cans may not be thrown entirely free of the carton but will simply be thrown partially out of the carton until they strike the rubber pad. The sound of the cans or other containers striking the pad is quite audible to the operator who can then shut off the motor and read the printout of the force cell. It is of course possible to provide a switch which will automatically shut off the motor upon contact of the carton containers with the rubber pad if that is a more desirable arrangement. The rubber pad cushions the contact of the containers against the end wall 28 to prevent breakage of the containers.

The TEFLON sheets 52 and 54 facilitate the sliding of the containers toward the rubber pad 56 to eliminate, or at least substantially reduce the possibility of, the failure point being affected by friction between the containers and the bottom wall 22 and the side wall 25. There is no need to provide such sheets on the wall 24 since the rotational forces of the apparatus maintain the carton in spaced relationship to the wall 24.

Although the foregoing description refers to the failure of the carton to hold its containers as the end point of the test, it will be understood that it is not necessary for the carton to fail by the tearing of its panels. As mentioned previously, the containers are held in place by the tight grip of the carton wrapper and usually also by the interfit of the bottom or top edges of the containers with small openings in the side panels of the carton. It is merely necessary in this test for the carton to no longer be able to hold the containers in place in order for the carton to be considered to have failed.

It should now be apparent that the invention is not necessarily limited to all the specific details described in connection with the preferred embodiment, but that changes to certain features of the preferred embodiment which do not alter the overall basic function and concept of the invention may be made without departing from the spirit and scope of the invention, as defined in the appended claims.

What is claimed is:

1. A test apparatus for determining the centrifugal force at which the contents of an open-ended carton having side panels are forced out an open end thereof, comprising:
    a support attached to a drive shaft;
    means for rotating the drive shaft and the attached support at varying speeds;
    means on the support for receiving an open-ended test carton arranged with one open end thereof facing the drive shaft and the other open end facing outwardly so that centrifugal force from the rotating support tends to cause the contents of the carton to move out said other open end;
    means for gripping the carton so as not to interfere with movement of the contents of the carton out said other open end; and
    means connected to the support and to the gripping means for measuring the force applied to the carton at the time the contents move out said other open end of the carton.

2. The apparatus of claim 1, wherein the carton gripping means comprises means for gripping end portions of the side panels of the carton nearest the drive shaft.

3. The apparatus of claim 2, wherein the gripping means are mounted on arms connected to a support body, the support body being connected to the force measuring means.

4. The apparatus of claim 3, wherein the support body contains means adjustably connecting the arms thereto.

5. The apparatus of claim 4, wherein the adjustable connecting means comprises notches in the support body, the notches facing away from the carton toward the drive shaft, the arms containing slots for receiving the support body at a notch thereof.

6. The apparatus of claim 2, wherein the carton gripping means comprise clamps which are adjustable to receive varying thicknesses of the end portions of side panels.

7. The apparatus of claim 6, wherein the clamps comprise roughened gripping surfaces for preventing slippage between the clamps and the side panels of the carton.

8. The apparatus of claim 2, wherein the support includes an end wall spaced from the other open end of the carton so that the contents of the carton closest to the end wall will strike the end wall upon moving out said other open end, the striking of the contents against the end wall indicating movement of the contents out of said other open end.

9. The apparatus of claim 8, including means for cushioning the end wall of the carton receiving means to prevent breakage of the contents of the carton upon striking the end wall.

10. The apparatus of claim 8, including friction reducing surfaces engaged by the contents of the carton upon leaving the carton and moving toward the end wall.

11. The apparatus of claim 8, wherein the support includes means for receiving a counterweight on the side of the drive shaft opposite the location of the test carton.

12. A method for determining the centrifugal force at which the contents of an open-ended carton having side panels are forced out an open end thereof, comprising:
    positioning a filled open-ended carton on a support adapted to rotate about a central point so that one open end thereof faces the central point and the other open end faces outwardly away from the central point;
    gripping end portions of the side panels of the carton so as not to interfere with movement of the contents of the carton out said other open end;
    rotating the support at increasing speeds of rotation until the centrifugal force created thereby causes the contents of the carton adjacent said other open end to move out said other open end; and
    measuring the centrifugal force applied to the carton at the time the contents move out said other open end of the carton.

13. The method of claim 12, wherein the other end of the carton is spaced from an end wall of the support so that the contents of the carton closest to the end wall will strike the end wall upon moving out said other open end.

* * * * *